United States Patent
Lie et al.

(10) Patent No.: US 11,346,837 B2
(45) Date of Patent: May 31, 2022

(54) METHOD AND APPARATUS FOR DETECTING A PROPERTY OF A LIQUID MEDIUM, UREA SENSOR SYSTEM, COMPUTER PROGRAM PRODUCT AND COMPUTER-READABLE STORAGE MEDIUM

(71) Applicant: TE Connectivity Norge AS, Blomersterdalen (NO)

(72) Inventors: Bjornar Berge Lie, Blomsterdalen (NO); Hakon Boe, Blomsterdalen (NO)

(73) Assignee: TE CONNECTIVITY NORGE AS, Blomsterdalen (NO)

( * ) Notice: Subject to any disclaimer, the term of this patent is extended or adjusted under 35 U.S.C. 154(b) by 0 days.

(21) Appl. No.: 17/071,466

(22) Filed: Oct. 15, 2020

(65) Prior Publication Data

US 2021/0116437 A1 Apr. 22, 2021

(30) Foreign Application Priority Data

Oct. 22, 2019 (EP) ..................... 19204681

(51) Int. Cl.
*G01N 33/493* (2006.01)
*G01N 29/024* (2006.01)
*G01N 29/032* (2006.01)

(52) U.S. Cl.
CPC ......... *G01N 33/493* (2013.01); *G01N 29/024* (2013.01); *G01N 29/032* (2013.01); *G01N 2291/011* (2013.01); *G01N 2291/015* (2013.01)

(58) Field of Classification Search
CPC .. G01N 33/493; G01N 29/024; G01N 29/032; G01N 2291/011; G01N 2291/015; G01N 29/48; G01N 2291/02433; G01N 2291/044; G01N 2291/045; G01N 29/32; G01N 29/343; G01N 29/4427; G01N 29/4463; G01N 2291/022; G01N 2291/102

See application file for complete search history.

(56) References Cited

U.S. PATENT DOCUMENTS

| 4,763,525 A | 8/1988 | Cobb |
| 2003/0172734 A1 | 9/2003 | Greenwood |
| 2007/0280712 A1* | 12/2007 | Holland ............... G03G 15/105 399/57 |

(Continued)

FOREIGN PATENT DOCUMENTS

| DE | 3210591 A1 | 10/1983 |
| DE | 102006013263 A1 | 9/2007 |

OTHER PUBLICATIONS

Extended European Search Report, European Application No. 19204681. 1-1020, European Filing Date, Mar. 11, 2020.

*Primary Examiner* — Peter J Macchiarolo
*Assistant Examiner* — John M Royston

(57) ABSTRACT

A method for detecting a property of a liquid medium comprises generating an ultrasonic pulse, receiving a first echo and a second echo of the ultrasonic pulse transmitted through the liquid medium, and generating a first amplitude signal for the first echo and a second amplitude signal for the second echo. The method includes calculating an amplitude signal ratio between the first amplitude signal and the second amplitude signal and determining a property signal representing the property of the liquid medium.

17 Claims, 2 Drawing Sheets

(56) References Cited

U.S. PATENT DOCUMENTS

| | | | |
|---|---|---|---|
| 2009/0178474 A1* | 7/2009 | Bailey | F02D 41/3809 |
| | | | 73/114.38 |
| 2012/0118059 A1 | 5/2012 | Reimer et al. | |
| 2019/0107513 A1 | 4/2019 | Kolesnikov et al. | |
| 2020/0386095 A1* | 12/2020 | Dugas | E21B 47/107 |

* cited by examiner

METHOD AND APPARATUS FOR DETECTING A PROPERTY OF A LIQUID MEDIUM, UREA SENSOR SYSTEM, COMPUTER PROGRAM PRODUCT AND COMPUTER-READABLE STORAGE MEDIUM

CROSS-REFERENCE TO RELATED APPLICATION

This application claims the benefit of the filing date under 35 U.S.C. § 119(a)-(d) of European Patent Application No. 19204681.1, filed on Oct. 22, 2019.

FIELD OF THE INVENTION

The invention relates to a method and an apparatus for detecting a property of a liquid medium and, more particularly, for detecting a property representative of disturbances in the liquid medium.

BACKGROUND

In methods and apparatuses for detecting a property of a liquid medium, the signal to noise ratio (SNR) is commonly determined. The SNR is, however, inaccurate and/or not suitable to accurately determine disturbances in the liquid medium. One problem of the art is a drift of a pulse generator and/or of a receiver, which may for instance occur because of a temperature change.

SUMMARY

A method for detecting a property of a liquid medium comprises generating an ultrasonic pulse, receiving a first echo and a second echo of the ultrasonic pulse transmitted through the liquid medium, and generating a first amplitude signal for the first echo and a second amplitude signal for the second echo. The method includes calculating an amplitude signal ratio between the first amplitude signal and the second amplitude signal and determining a property signal representing the property of the liquid medium.

BRIEF DESCRIPTION OF THE DRAWINGS

The invention will now be described by way of example with reference to the accompanying Figures, of which.

DETAILED DESCRIPTION OF THE EMBODIMENT(S)

In the following, the invention is described by way of the accompanying figures, which describe exemplary embodiments of the present invention. Technical features of those exemplary embodiments may be arbitrarily combined with each other. Further, the exemplary embodiments do not limit a possible scope of protection, which is defined by the claims.

Figure 1:
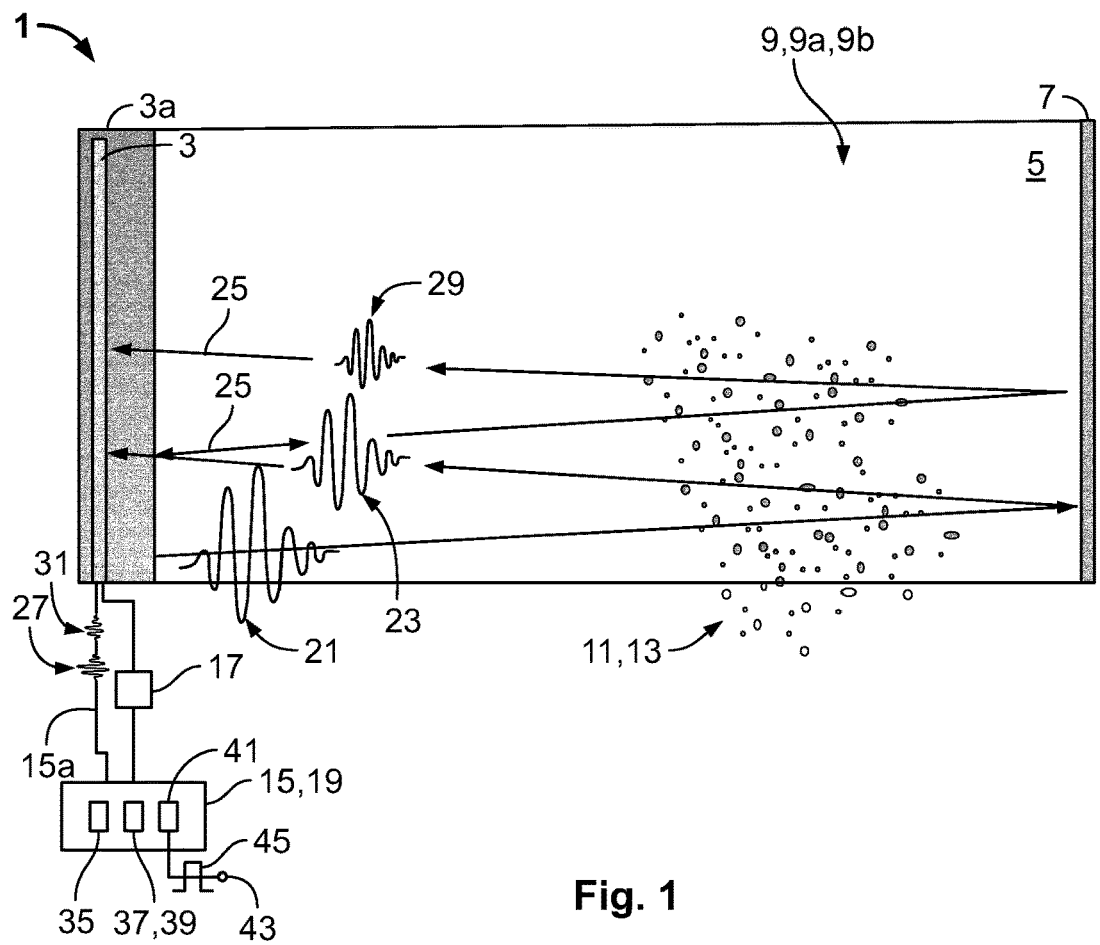
FIG. 1 is a schematic diagram of an apparatus according to an embodiment.

An apparatus 1 according to an embodiment is shown in FIG. 1. The apparatus 1 comprises a pulse generator or transducer 3, which is provided in a transducer housing 3a.

The transducer 3 is located adjacent to a sample volume 5, wherein opposite the transducer 3, a reflector 7 is provided.

In the sample volume 5, as shown in FIG. 1, a liquid medium 9 in the form of an aqueous solution 9a is provided, wherein disturbances 11 in the form of bubbles 13 may occur in the aqueous solution 9a. The aqueous solution 9a, in an embodiment, may be a urea solution 9b. In an embodiment, a urea sensor system for determining a property of the urea solution 9b, such as disturbances 11 in the urea solution 9b, comprises the apparatus 1.

The apparatus 1, as shown in FIG. 1, comprises a calculator unit 15, which, in the embodiment shown, is connected to an electronic control unit 17 and to the transducer 3. The calculator unit 15 may also be a controller 19 that controls an output of the electronic control unit 17, which in turn drives transducer 3, i.e. provides the transducer 3 with an electronic signal, which is converted into an ultrasonic pulse 21 by the transducer 3. In another embodiment, there may be provided a single and individual pulse generator and a single and individual receiver, which are not combined in one element. In the embodiment shown in FIG. 1 those two are combined in the transducer 3.

The ultrasonic pulse 21 is transmitted through the aqueous solution 9a, is reflected at the reflector 7, and returns as a first echo 23 to the transducer 3, as shown in FIG. 1. There, a portion 25 of the first echo 23 is absorbed in the transducer 3 and generates a first electrical or amplitude signal 27 that represents the first echo 23. This is indicated as a signal on a data line 15a of the calculator unit 15.

The first echo 23 is also reflected at the transducer and is transmitted towards the reflector 7 again. There, it is reflected and returns to the transducer 3 as a second echo 29 shown in FIG. 1. Again, a portion 25 of the second echo 29 is absorbed in the transducer 3 and generates a second electrical signal 31. Also, the second electrical or amplitude signal 31 is schematically shown on the data line 15a. As the second echo 29 is attenuated, the second electrical signal 31 is smaller than the first electrical signal 27. The time it takes for the ultrasonic pulse 21 from its generation to its arrival at the transducer 3 as the first echo 23 is a time of flight 55.

A measured speed of sound can be calculated and a measured speed of sound signal provided representing the measured speed of sound. The speed of sound may be calculated by the time of flight 55 and a known distance the ultrasonic pulse 21 traveled. The calculating unit 15 may provide a calculator that divides the distance traveled by the time of flight 55 of the first echo 23.

The calculator unit 15, as shown in FIG. 1, may comprise a comparator unit 35, a storage module 37, comprising a lookup table 39 as well as an output unit 41 that comprises an output port 43 for providing a calculated speed of sound signal 45. The calculated speed of sound signal 45 is illustrated by a rectangular pulse on the output port 43. The calculator unit 15 may be embodied as a field programmable gate area, a microcontroller, or any suitable integrated circuit. The calculator unit 15 calculates the first amplitude signal 27 and the second amplitude signal 31.

When sending an ultrasonic pulse 21 through a liquid medium 9, for example through an aqueous solution 9a, bubbles 13, in particular gas bubbles and other disturbances will affect the pulse 21. A signal may be disturbed to such an extent that further measurements based on transmitting and receiving a reflected ultrasonic pulse 21 may not be performed accurately any longer. Within this disclosure, the features liquid medium 9 and aqueous solution 9a may be replaced by each other. Thus, an embodiment denoting an aqueous solution 9a may be applied to a more general liquid medium 9 as well.

As indicated in FIG. 1, the disturbances 11 in the form the bubbles 13 do influence the ultrasonic pulse 21 as well as the first echo 23 and the second echo 29, in particular the signal strength of the first 27 and the second electrical signal 31, as the ultrasonic pulse 17 as well as the first echo 23 and the second echo 29 are attenuated when being transmitted through the aqueous solution 9a and the bubbles 13 therein.

Figure 2:
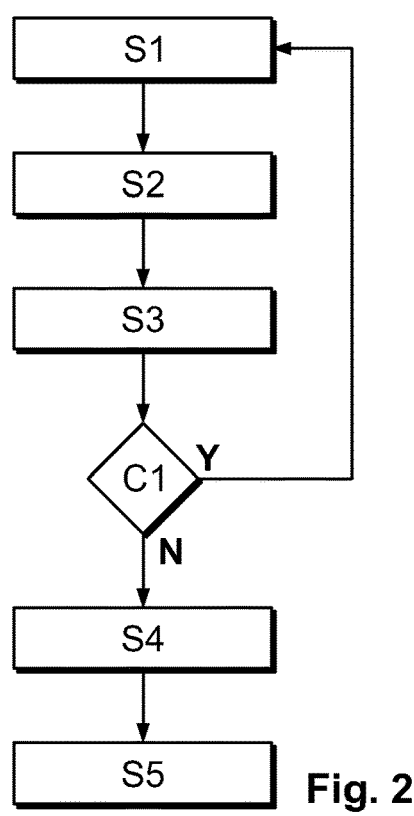
FIG. 2 is a flowchart of a method according to an embodiment.

A method according to an embodiment is shown in FIG. 2. In step one S1, the ultrasonic pulse 21 is generated. In step two S2, the first echo 23 and the second echo 29 are received by the transducer 3 and converted into the corresponding first electrical signal 27 and the second electrical signal 31. Subsequently, in step three S3 an amplitude signal ratio between the amplitude signal of the first echo 23 and the amplitude signal of the second echo 29 is calculated at the calculator unit 15. The same or an additional calculating unit 15 may perform the calculation of the amplitude signal ratio.

Based on this amplitude signal ratio, as shown in FIG. 2, a condition one C1 is checked and verified. At least one property signal is determined by the calculator unit 15, wherein said property signal represents the property of the liquid medium 9. In particular, the property signal may represent the presence of any disturbance 11 in the liquid medium 9. At the calculator unit 15, the amplitude signal ratio is compared with a predetermined amplitude ratio threshold and it is checked whether the amplitude ratio signal exceeds the amplitude ratio threshold. If this is the case (branch indicated with 'Y') the entire method is restarted with step one S1 and/or an alert signal is provided.

This embodiment may accurately determine whether the property of the liquid medium 9 may be reliably measured or not, e.g. because of too much disturbances 11, like too many bubbles 13 present in the liquid medium 9, which would hinder an accurate measurement. In particular in case of the urea solution 9b, where urea tends to produce bubbles 13 caused by vibrations, the extent of the number of bubbles 13 generated in the liquid medium 9 may constitute a critical parameter and needs to be monitored. This embodiment allows indicating such an excessive presence of bubbles 13 or more general: the excessive presence of disturbances 11 or even more general of the property of the liquid medium 9 exceeding a predetermined threshold. One object of this embodiment is to indicate the exceeded threshold, wherein the outcome of this comparison may trigger further method steps, as e.g. the re-initialization or restart of the method. It is also conceivable that a detected exceeded threshold may initiate a further method step in which the number of bubbles in the liquid medium 9, in particular a urea solution 9b, is reduced.

If the amplitude ratio threshold is not exceeded (branch indicated with 'N'), the method continues with step four S4, in which a compensation factor is determined by the calculator unit 15, which is subsequently handed over to step five S5 in which the method determines a calculated speed of sound. The calculated speed of sound in the liquid medium 9 may be determined at least based on the measured speed of sound and the compensation factor. The compensation factor cancels out properties and provides more accurate measurements in the disturbed liquid media 9. The properties of the ultrasonic transducer 3 are canceled out, i.e. do not influence the measurement. This may e.g. be advantageous in case of temperature drift, which would otherwise alter the properties of the transducer 3.

In other embodiments, the predetermined calibration signal ratio may be determined during calibration and/or provided in a storage medium. Thus, the predetermined calibration signal ratio may be determined prior to the ultrasonic measurement or provided in and read from a storage location, where it has been stored prior to the measurement. The calculated speed of sound may further depend on an empirically found variable. The calibration value may in particular depend on the liquid medium 9. Thus, different liquid media 9 may have different calibration values.

As mentioned above, the embodiment of the present disclosure may particularly be applied in the field of urea solutions 9b applied in diesel engines for cleaning diesel exhaust fumes. Commonly, speed of sound measurements may be applied for detecting the type and/or quality of the liquid medium 9, whereas in particular applying urea, said aqueous solution tends to produce bubbles 11, which renders measurements of the speed of sound inaccurate. It is therefore advantageous to precisely and accurately determine whether bubbles 11 are present in the urea solution 9b and to what extent. It is further advantageous to additionally cancel out the influence of present bubbles when determining the speed of sound in the liquid medium 9.

This flowchart only describes an exemplary embodiment of the inventive method. In different embodiments, additional steps may be provided, like e.g. outputting the determined calculated speed of sound signal and the like. Similarly, more conditions may be checked in different embodiments of the method.

In another embodiment, the method further comprises the step of selecting one liquid medium 9 out of a list of liquid media, and providing a corresponding calibration ratio depending on the selected liquid medium 9. According to this embodiment, the liquid medium 9 is known prior to the measurement and specified before a measurement. Said list of liquid media may be provided in the storage module 37 of the calculating unit 15. The storage module 37 may further comprise calibration ratios that correspond to a liquid medium 9. The liquid media and corresponding calibration ratios may be correlated to each other in the lookup table 39.

Another embodiment of the method comprises the step of determining a type and/or composition of a liquid medium 9, through which the ultrasonic pulse 21 is transmitted, based on the calculated speed of sound signal. In order to determine the type of liquid medium 9, the calculated speed of sound signal is compared with a predetermined and/or stored list of the speed of sound signals. Thus, a list of possible liquid media is provided, e.g. in the lookup table 39, wherein additionally the speed of sound in those possible liquid media is related to those types of liquid media. By comparing the calculated speed of sound signal with a previously stored speed of sound signals, it is thus possible to assign the correct liquid medium.

The method thus allows determining a) a type of the liquid medium 9 and/or b) a specific composition of the liquid medium 9. In particular, in case of an urea solution 9b this embodiment may be applied to measure an urea concentration independent on any transducer drifts or temperature influences as well as independent on disturbed conditions as for instance the presence of bubbles 13. This embodiment further provides a speed of sound in the liquid medium 9 that it would be obtained without any disturbance 11.

The present invention can be embodied as a computer program product and a non-transitory computer-readable storage medium by comprising instructions which, when executed by a computer, cause the computer to carry out the steps of the inventive method.

Figure 3:
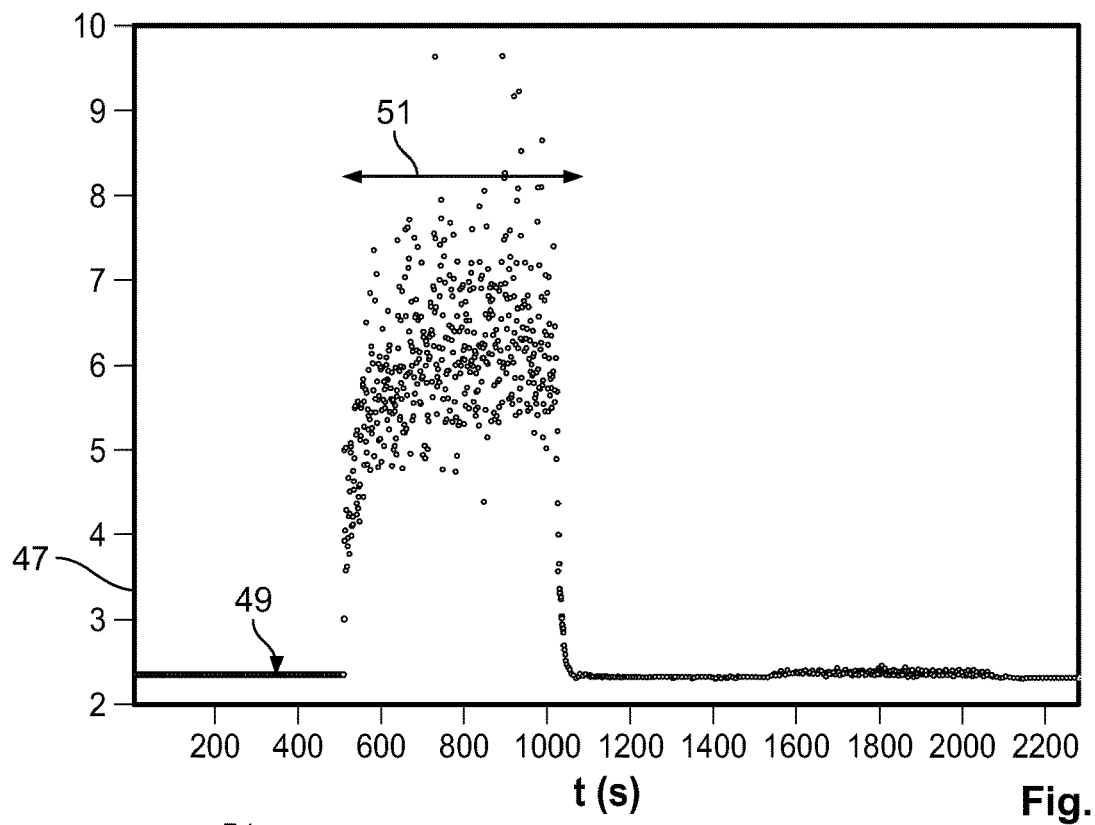
FIG. 3 is a graph of attenuation versus time.
Figure 4:
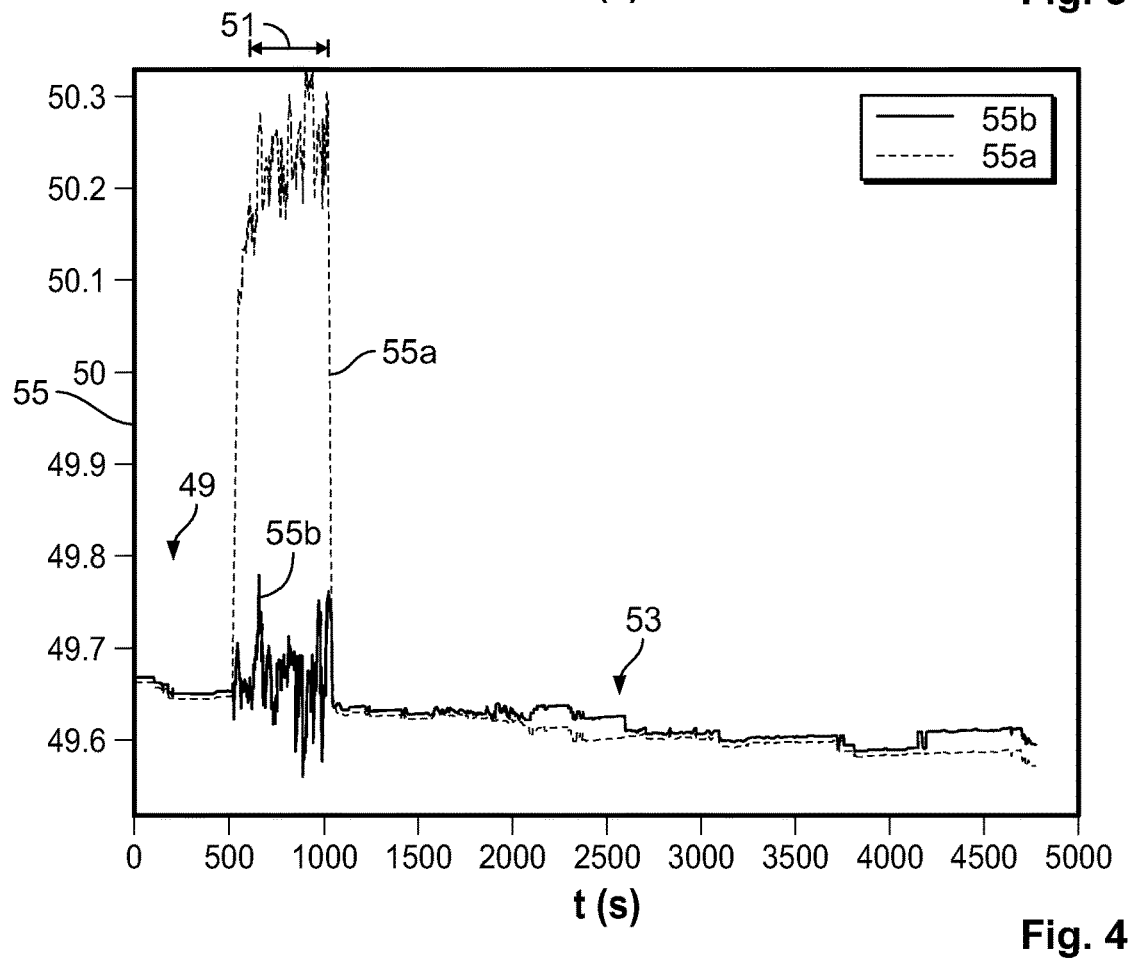
FIG. 4 is a graph of time of flight versus time.

In FIG. 3 and FIG. 4, two exemplary measurements are shown to illustrate the effect of disturbances to an ultrasound measurement.

FIG. 3 shows an attenuation 47 depending on a time t. The attenuation 47 is functionally dependent on the amplitude signal ratio between the amplitude signal 27 of the first echo 23 and the amplitude signal 31 of the second echo 29. In a first region 49, no disturbances 11 are present in the liquid medium 9, wherein in a second region 51, disturbances 11 were present and clearly increased the attenuation 47. In a third region 53 again no disturbances 11 are present.

FIG. 4 shows the time of flight 55, having the unit of a time and corresponding to the time the ultrasonic pulse 21 takes for traveling through the sample volume 5 until it arrives again at the transducer 3, which is drawn over the time t. The graph shows a measured time of flight 55a which is correlated with the attenuation 47 shown in FIG. 3. This correlation is applied to correct the time of flight 55a, wherein after correction using the attenuation 47, a corrected time of flight 55b is obtained. The corrected time of flight 55b is drawn with a thicker solid line. The increased time of flight 55 in the second region 51 may be explained by a higher speed of sound in bubbles 13 comprising a gaseous phase like air.

FIG. 4 clearly shows that, even in the case of an increased attenuation from approximately 2.5 to a value of on average 6, the time of flight 55 may be accurately corrected to correspond to the time of flight 55 in the first region 49 and the third region 53, in which no disturbances 11 are present. Consequently, the method allows determining a time of flight 55, and consequently a speed of sound in the liquid medium 9, which would be measured if no disturbances 11 were present. Properties of a pristine liquid medium 9 may thus also be acquired, respectively calculated if the liquid medium 9 already contains disturbances 11, e.g. in the form of bubbles 13.

What is claimed is:

1. A method for detecting a property of a liquid medium, comprising:
   generating an ultrasonic pulse;
   receiving a first echo and a second echo of the ultrasonic pulse transmitted through the liquid medium, the second echo is a reflection of the first echo;
   generating a first amplitude signal for the first echo and a second amplitude signal for the second echo;
   calculating an amplitude signal ratio between the first amplitude signal and the second amplitude signal; and
   determining a property signal representing the property of the liquid medium.

2. The method of claim 1, wherein the property is representative of a plurality of disturbances in the liquid medium.

3. The method of claim 1, further comprising determining a time of flight for the first echo.

4. The method of claim 3, wherein the time of flight is used to calculate a measured speed of sound and provide a measured speed of sound signal representing the measured speed of sound.

5. The method of claim 4, further comprising determining a compensation factor based on the amplitude signal ratio and a predetermined calibration ratio.

6. The method of claim 5, further comprising determining a calculated speed of sound in the liquid medium at least based on the measured speed of sound and the compensation factor and providing a calculated speed of sound signal representing the calculated speed of sound.

7. The method of claim 6, wherein the calculated speed of sound depends on an empirically found variable.

8. The method of claim 1, further comprising comparing the amplitude signal ratio with a predetermined amplitude ratio threshold, the method is re-initiated and/or an alert signal is provided if the amplitude signal ratio exceeds the predetermined amplitude ratio threshold.

9. The method of claim 5, wherein the predetermined calibration ratio depends on the liquid medium.

10. The method of claim 5, further comprising selecting a liquid medium out of a list of liquid media, the predetermined calibration ratio depends on the selected liquid medium.

11. The method of claim 6, further comprising determining a type and/or a composition of the liquid medium through which the ultrasonic pulse is transmitted based on the calculated speed of sound signal.

12. The method of claim 11, wherein the calculated speed of sound signal is compared with a predetermined and/or stored list of speed of sound signals for determining the type of the liquid medium.

13. An apparatus for detecting a property of a liquid medium, comprising:
   a pulse generator configured to generate an ultrasonic pulse;
   a receiver configured to receive a first echo and a second echo of the ultrasonic pulse transmitted through the liquid medium, the second echo is a reflection of the first echo; and
   a calculator unit configured to find and calculate a first amplitude signal for the first echo and a second amplitude signal for the second echo, and to calculate an amplitude signal ratio between the first amplitude signal and the second amplitude signal to determine a property signal representing the property of the liquid medium.

14. A urea sensor system for determining a property of a urea solution, comprising:
   an apparatus including a pulse generator configured to generate an ultrasonic pulse, a receiver configured to receive a first echo and a second echo of the ultrasonic pulse transmitted through the liquid medium, the second echo is a reflection of the first echo, and a calculator unit configured to find and calculate a first amplitude signal for the first echo and a second amplitude signal for the second echo, the calculator unit configured to calculate an amplitude signal ratio between the first amplitude signal and the second amplitude signal to determine a property signal representing the property of the liquid medium.

15. A non-transitory computer program product, comprising:
   a plurality of instructions that, when executed by a computer, perform the steps of:
   generating an ultrasonic pulse;
   receiving a first echo and a second echo of the ultrasonic pulse transmitted through the liquid medium, the second echo is a reflection of the first echo;
   generating a first amplitude signal for the first echo and a second amplitude signal for the second echo;
   calculating an amplitude signal ratio between the first amplitude signal and the second amplitude signal; and
   determining a property signal representing the property of the liquid medium.

16. A non-transitory computer-readable storage medium comprising:
   a plurality of instructions that, when executed by a computer, perform the steps of:

generating an ultrasonic pulse;

receiving a first echo and a second echo of the ultrasonic pulse transmitted through the liquid medium, the second echo is a reflection of the first echo;

generating a first amplitude signal for the first echo and a second amplitude signal for the second echo;

calculating an amplitude signal ratio between the first amplitude signal and the second amplitude signal; and determining a property signal representing the property of the liquid medium.

17. A method for detecting a property of a liquid medium, comprising:

generating an ultrasonic pulse;

receiving a first echo and a second echo of the ultrasonic pulse transmitted through the liquid medium;

generating a first amplitude signal for the first echo and a second amplitude signal for the second echo;

calculating an amplitude signal ratio between the first amplitude signal and the second amplitude signal;

determining a property signal representing the property of the liquid medium;

determining a time of flight for the first echo, the time of flight is used to calculate a measured speed of sound and provide a measured speed of sound signal representing the measured speed of sound;

determining a compensation factor based on the amplitude signal ratio and a predetermined calibration ratio; and selecting a liquid medium out of a list of liquid media, the predetermined calibration ratio depends on the selected liquid medium.

* * * * *